(12) United States Patent
Yoo et al.

(10) Patent No.: US 10,932,756 B2
(45) Date of Patent: Mar. 2, 2021

(54) ULTRASONIC IMAGING APPARATUS AND CONTROL METHOD THEREOF

(71) Applicant: SAMSUNG MEDISON CO., LTD., Gangwon-do (KR)

(72) Inventors: Jun Sang Yoo, Seongnam-si (KR); Kwang-Hee Lee, Incheon (KR); Sung-Yoon Kim, Namyangju-si (KR); Jong Sik Kim, Seoul (KR); Gil-Ju Jin, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 903 days.

(21) Appl. No.: 15/166,071

(22) Filed: May 26, 2016

(65) Prior Publication Data

US 2016/0361045 A1    Dec. 15, 2016

(30) Foreign Application Priority Data

Jun. 15, 2015    (KR) ........................ 10-2015-0084057

(51) Int. Cl.
*A61B 8/00*    (2006.01)
*A61B 8/08*    (2006.01)
(Continued)

(52) U.S. Cl.
CPC .............. *A61B 8/54* (2013.01); *A61B 8/0808* (2013.01); *A61B 8/0816* (2013.01); *A61B 8/0825* (2013.01); *A61B 8/0866* (2013.01); *A61B 8/0883* (2013.01); *A61B 8/0891* (2013.01); *A61B 8/14* (2013.01); *A61B 8/4245* (2013.01);
(Continued)

(58) Field of Classification Search
None
See application file for complete search history.

(56) References Cited

U.S. PATENT DOCUMENTS

2004/0097806 A1*    5/2004    Hunter ............... A61B 1/00071
                                                            600/434
2005/0004465 A1*    1/2005    Abuhamad .......... A61B 8/0866
                                                            600/443
(Continued)

FOREIGN PATENT DOCUMENTS

EP    2296011 A2    3/2011
EP    2679158 A1    1/2014
(Continued)

OTHER PUBLICATIONS

Extended European Search Report dated Oct. 21, 2016 issued in European Patent Application No. 15178609.2.

*Primary Examiner* — Pascal M Bui Pho
*Assistant Examiner* — Yi-Shan Yang
(74) *Attorney, Agent, or Firm* — Morgan, Lewis & Bockius LLP

(57) ABSTRACT

Disclosed herein is an ultrasonic imaging apparatus and a control method thereof. The ultrasonic imaging apparatus includes an acquisition unit configured to acquire a volume data of an object and a process configured to determine whether an acquisition position of the volume data is within an allowable range by using pre-stored landmark information and configured to acquire a plurality of reference planes from the volume data when the acquisition position of the volume data is within the allowable range.

19 Claims, 21 Drawing Sheets

(51) Int. Cl.
  *A61B 8/14* (2006.01)
  *G06T 7/73* (2017.01)

(52) U.S. Cl.
  CPC ............... *A61B 8/46* (2013.01); *A61B 8/483* (2013.01); *A61B 8/523* (2013.01); *G06T 7/73* (2017.01); *G06T 2207/10132* (2013.01); *G06T 2207/30016* (2013.01); *G06T 2207/30244* (2013.01)

(56) References Cited

U.S. PATENT DOCUMENTS

| | | | |
|---|---|---|---|
| 2009/0093717 A1 | 4/2009 | Carneiro et al. | |
| 2010/0307516 A1* | 12/2010 | Neubauer | A61B 5/103 128/898 |
| 2011/0054324 A1* | 3/2011 | Lee | A61B 8/0808 600/443 |
| 2013/0057547 A1* | 3/2013 | Hwang | G06T 7/75 345/420 |
| 2013/0072797 A1* | 3/2013 | Lee | A61B 8/466 600/443 |
| 2013/0324849 A1* | 12/2013 | Park | A61B 8/463 600/440 |
| 2014/0100440 A1* | 4/2014 | Cheline | A61B 5/0066 600/407 |
| 2014/0153358 A1* | 6/2014 | Balakrishnan | G01S 7/52074 367/7 |
| 2015/0190653 A1* | 7/2015 | Bharat | A61N 5/1027 600/7 |
| 2015/0302638 A1* | 10/2015 | Jago | A61B 8/0866 345/420 |
| 2017/0367685 A1* | 12/2017 | Zou | A61B 8/0808 |

FOREIGN PATENT DOCUMENTS

| | | |
|---|---|---|
| WO | 2004/093687 A1 | 11/2004 |
| WO | 2014/080319 A1 | 5/2014 |

\* cited by examiner

ULTRASONIC IMAGING APPARATUS AND CONTROL METHOD THEREOF

CROSS-REFERENCE TO RELATED APPLICATION

This application claims the benefit of Korean Patent Application No. 10-2015-0084057, filed on Jun. 15, 2015 in the Korean Intellectual Property Office, the disclosure of which is incorporated herein by reference.

BACKGROUND

1. Field

Embodiments of the present disclosure relate to an ultrasonic imaging apparatus configured to be used easily, and a control method of the same.

2. Description of the Related Art

An ultrasonic imaging apparatus irradiates ultrasound signals to a target part inside an object from the surface of an object, and noninvasively acquires section images about soft tissue of the object or images about blood vessels of the object by using echo ultrasound signals reflected from the object.

An ultrasonic imaging apparatus is compact, inexpensive, and displaying a diagnostic imaging immediately as compared with another type of diagnostic imaging apparatus, e.g., X-ray device, Magnetic Resonance Image (MRI), diagnostic nuclear medical apparatus. In addition, the ultrasonic imaging apparatus is safe because there is no risk of radiation exposure. Therefore, the ultrasonic imaging apparatus is widely used in medical examination at cardiology, abdomen, urology, and maternity clinics.

An ultrasonic imaging apparatus is widely used to diagnose the condition of fetus, but there are difficulties in acquiring an appropriate ultrasound image to diagnosis the condition of fetus.

SUMMARY

Therefore, it is an aspect of the present disclosure to provide an ultrasonic imaging apparatus capable of easily extracting a reference plane and a control method of the ultrasonic imaging apparatus.

Additional aspects of the disclosure will be set forth in part in the description which follows and, in part, will be obvious from the description, or may be learned by practice of the disclosure.

In accordance with one aspect of the present disclosure, an ultrasonic imaging apparatus includes an acquisition unit configured to acquire a volume data of an object and a processor configured to determine whether an acquisition position of the volume data is within an allowable range by using pre-stored landmark information and configured to acquire a plurality of reference planes from the volume data when the acquisition position of the volume data is within the allowable range.

The pre-stored landmark information may include a landmark about at least one of reference plane among the plurality of reference planes.

The pre-stored landmark information may include a landmark commonly existed in the plurality of reference planes and a landmark distinctively existed in each reference plane of the plurality of the reference planes. For example, the pre-stored landmark information may include at least one of Cavum septum pellucidum (CSP), Cerebellum, Choroid plexus, Lateral ventricle, Cisterna magna, and Thalami.

The processor may determine whether the acquisition position of the volume data is within the allowable range by comparing a similarity between at least one plane extracted from the volume data and the landmark about the reference plane.

The processor may provide a first feedback to a user when the acquisition position of the volume data is determined to be within the allowable range. At this time, the first feedback may include at least one of a tactile feedback, a visual feedback and an auditory feedback.

The processor may provide a second feedback to a user when the acquisition position of the volume data is determined to be out of the allowable range. At this time, the processor may estimate a relative position of the volume data with respect to the allowable range, and may generate the second feedback based on the relative position. In addition, the second feedback may be differently generated according to the relative position of the volume data with respect to the allowable range.

The processor may provide a third feedback when the volume data is acquired by scanning an object asymmetrically.

The allowable range may include at least two planes among the plurality of reference planes.

In accordance with another aspect of the present disclosure, a control method of an ultrasonic imaging apparatus includes acquiring a volume data of an object, determining whether an acquisition position of the volume data is within an allowable range by using pre-stored landmark information, and extracting a plurality of reference planes from the volume data when the acquisition position of the volume data is within the allowable range.

The determining of acquisition position may include comparing a similarity between at least one plane extracted from the volume data and landmark information of the reference plane, and determining that the position of the volume data is within the allowable range when the similarity is larger than a threshold.

The control method may further include providing a first feedback to a user when the acquisition position of the volume data is within the allowable range.

The control method may further include estimating a relative position of the volume data with respect to the allowable range when the acquisition position of the volume data is determined to be out of the allowable range, and generating and providing a second feedback based on the relative position.

The control method may further include extracting a plane from the volume data, determining of symmetry of the extracted plane, and providing a third feedback when the extracted plane is asymmetrical.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter 'ultrasound image' may represent an image of an object acquired by using ultrasonic waves, and 'an object' may represent a human, an animal or a part of a human or animal. The ultrasound image may include a three dimensional (3D) volume image as well as a two dimensional (2D) cross sectional image.

An object may include liver, heart, uterus, brain, breasts, or blood vessel, and hereinafter for the convenience of description, the object is limited to fetus inside a mother.

In addition, hereinafter a user may be a medical professional, e.g., a doctor, a nurse, a medical technologist or a medical imaging professional, and a technician capable of serving medical apparatuses may become the user, but is not limited thereto.

Figure 1:
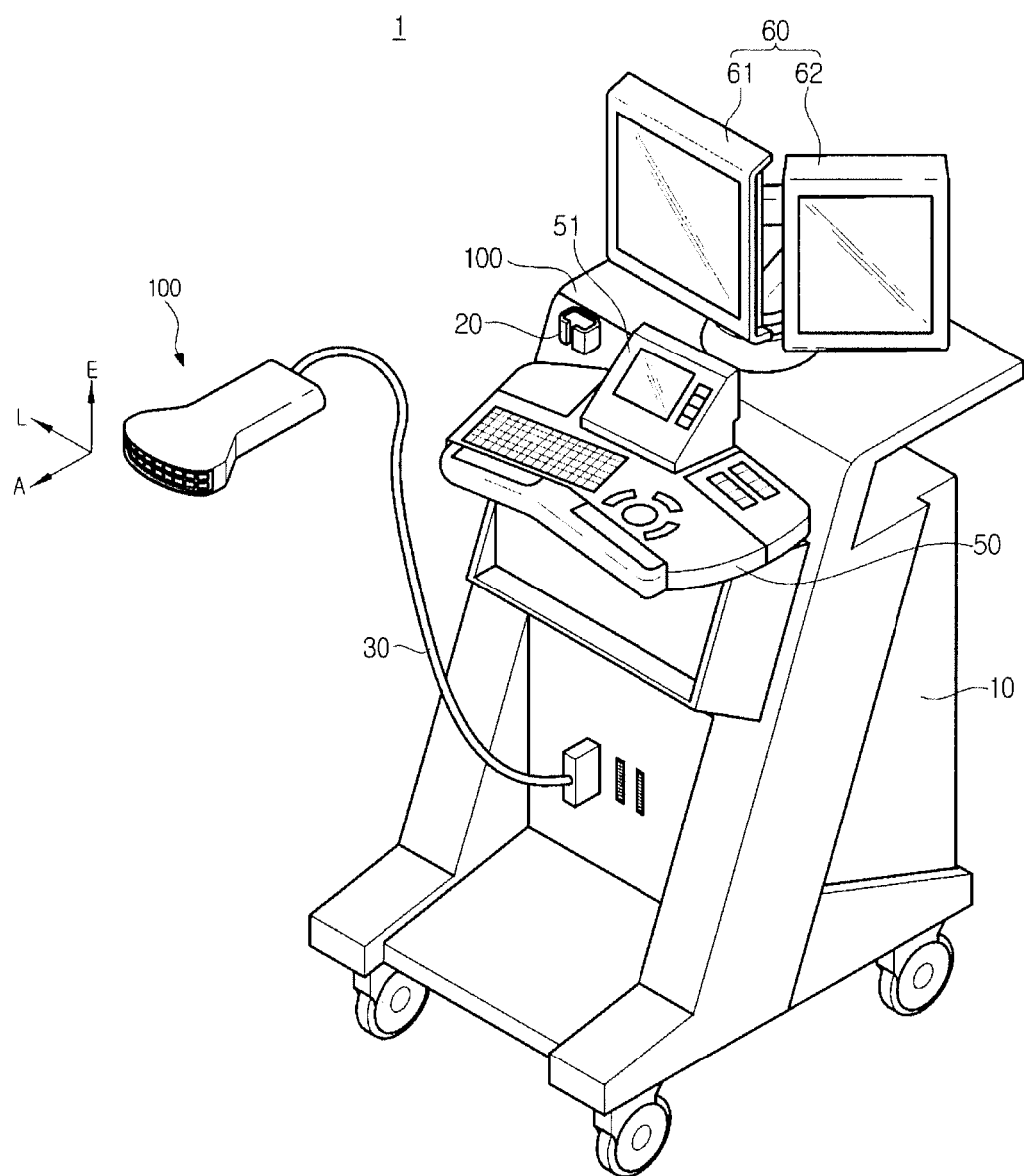
FIG. 1 is a perspective view illustrating an exterior of an ultrasonic imaging apparatus according to an embodiment of the present disclosure.
Figure 2:
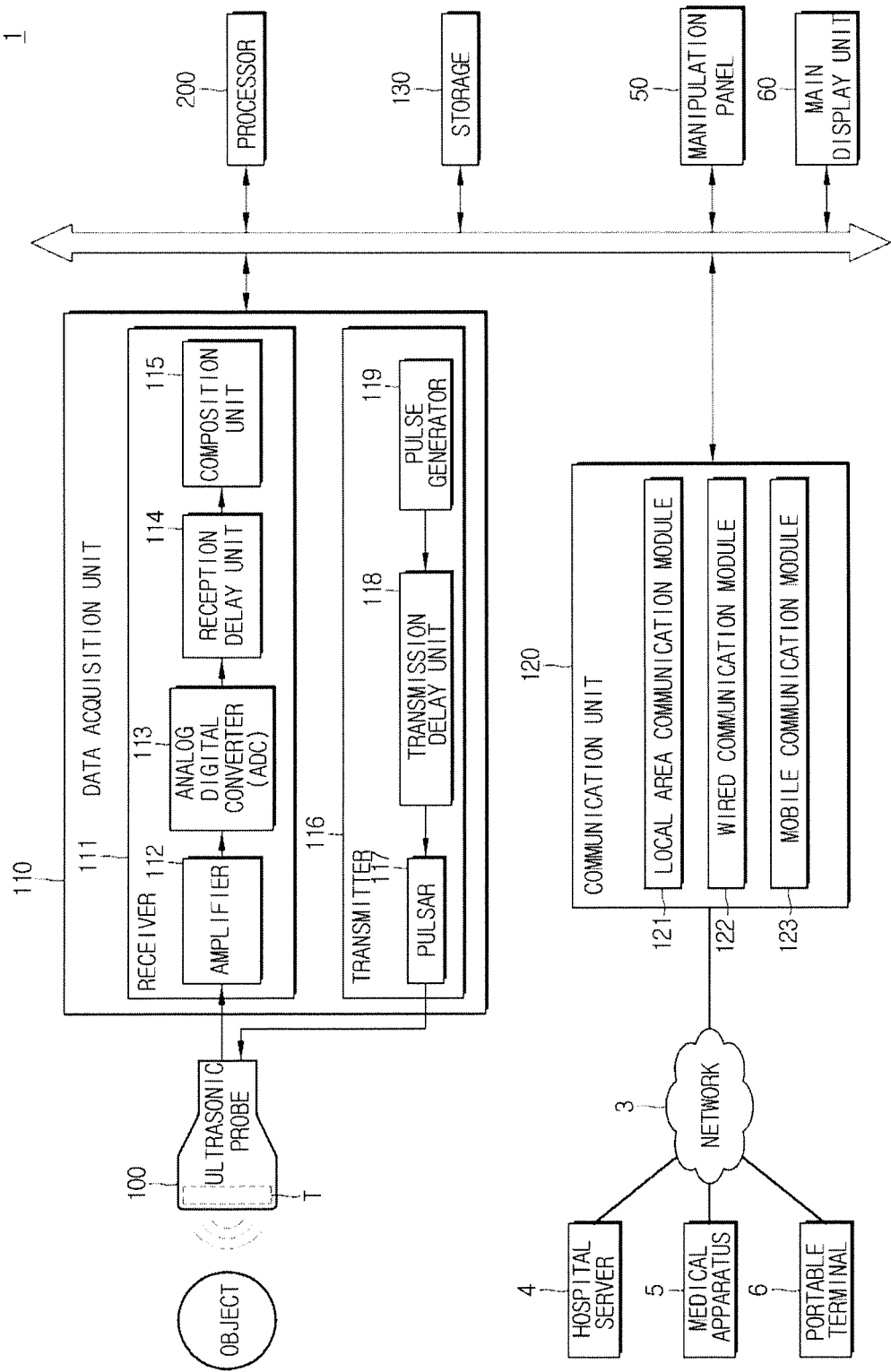
FIG. 2 is a control block diagram illustrating an ultrasonic imaging apparatus according to an embodiment of the present disclosure.

FIG. 1 is a perspective view illustrating an exterior of an ultrasonic imaging apparatus according to an embodiment of the present disclosure and FIG. 2 is a control block diagram illustrating an ultrasonic imaging apparatus according to an embodiment of the present disclosure.

Referring to FIGS. 1 and 2, an ultrasonic imaging apparatus 1 may include a body 10, an ultrasonic probe 100, a manipulation panel 50, and a display unit 60.

The ultrasonic probe 100 may be a part configured to scan an object ob by making contact with a surface of the ob, and may transmit ultrasonic signal to the object ob according to a driving signal or may receive an echo signal reflected from the object ob.

A direction, which is scanned by the ultrasonic probe 100, may be defined as an axis direction A, a lateral direction L, and an elevation direction E. The direction A may represent a direction in which ultrasonic waves are irradiated, the direction L may represent a direction in which transducers T form a row, and the direction E may represent a direction perpendicular to the direction A and the direction L.

The ultrasonic probe 100 may include a plurality of transducers T. The transducer T may convert an ultrasound signal into an electrical signal or vice versa.

Each transducer T may be implemented by a magnetostrictive ultrasonic transducer using the magnetostrictive effect of a magnetic material, a piezoelectric ultrasonic transducer using the piezoelectric effect of a piezoelectric material, piezoelectric micromachined ultrasonic transducer (pMUT) or a capacitive micromachined ultrasonic transducer (hereinafter referring to cMUT) that transmits and receives ultrasonic waves using vibration of several hundreds or thousands of micromachined thin films.

The transducers T may be arranged in an array. For example, the transducers T may be arranged in a linear array, in a convex array, in a phased array, or in a sector array. In addition, the transducers T may be arranged in a multiple dimensional array, e.g., M*N array.

When the transducers T are arranged in one dimension, the ultrasonic probe 100 may acquire an ultrasonic signal of a space of an object by swing the array of the transducers T in the direction E, and when the transducers T are arranged in multiple dimensional array, the ultrasonic probe 100 may acquire an ultrasonic signal of a space of an object by a single transmission of ultrasonic waves.

The ultrasonic probe 100 may be connected to the body 10 of the ultrasonic imaging apparatus 1 via a cable 30 to receive various signals, which are needed for control of the ultrasonic probe 100, from the body 10. In addition, the ultrasonic probe 100 may transmit an analog signal or a digital signal corresponding to an echo signal received by the ultrasonic probe 100, to the body 10.

A data acquisition unit 110 may form an ultrasonic signal transmitted from the ultrasonic probe 100 or may composite an echo signal outputted from the ultrasonic probe 100. As mentioned above, an echo signal which is composited in the data acquisition unit 110 may be referred to as ultrasound data, and an ultrasound data about a 3D volume may be referred to as a volume data. When the generated ultrasound data corresponds to a cross-section of the object, a volume data may be configured with a plurality of ultrasound data of different cross sections.

The data acquisition unit 110 may include a receiver 111 and a transmitter 116. The transmitter 116 may supply a driving signal to the ultrasonic probe 100, and may include a pulse generator 119, a transmission delay unit 118, and a pulsar 117.

The pulse generator 119 may generate a pulse to form transmission ultrasonic waves according to a certain Pulse Repetition Frequency (PRF), and the transmission delay unit 118 may apply a delay time to a pulse to determine transmission directionality. Each pulse in which a delay time is applied may correspond to each transducer T included in the ultrasonic probe 100. The pulsar 117 may apply a driving signal or a driving pulse, which is a timing corresponding to each pulse in which a delay time is applied.

The receiver 111 may generate ultrasound data by processing an echo signal received from the ultrasonic probe 100, and may include an amplifier 112, an Analog Digital converter (ADC) 113, a reception delay unit 114, and a composition unit 115. The amplifier 112 may amplify an echo signal inputted through a channel, and the ADC 113 may perform analog-digital conversion on an amplified echo signal. The reception delay unit 114 may apply a delay time to an echo signal, which is converted into a digital, to determine reception directionality, and the composition unit 115 may generate ultrasound data by compositing an echo signal, which is processed by the reception delay unit 114. Meanwhile, the receiver 111 may not include the amplifier 112 according to the type of the implementation of the receiver 111. That is, when the sensibility of the ultrasonic probe 100 is improved or when the number of processing bits of the ADC 113 is improved, the amplifier 112 may be omitted.

Meanwhile, FIG. 1 illustrates a case in which the ultrasonic probe 100 and the data acquisition unit 110 are separately provided, but the ultrasonic probe 100 and the data acquisition unit 110 may be integrally provided.

The manipulation panel 50 may receive an input of a control command related to operations of the ultrasonic imaging apparatus 1. The user may input a diagnosis start command, a command for selecting an area to be diagnosed, a command for selecting a diagnosis type, and a command for selecting a display mode of an image to be output, through the manipulation panel 50. The display mode may include an Amplitude mode (A mode), a Brightness mode (B mode), a Doppler mode (D mode), an Elastography mode (E mode), and a Motion mode (M mode).

The manipulation panel 50 may receive an input of a command of generating a 3D volume image, and a command of extracting a reference plane. In addition, the user may input direction and location information which are needed to extract a reference plane by using the manipulation panel 50.

In addition, the manipulation panel 50 may be implemented by button input devices, e.g., push button, membrane button, and touch input device, e.g., touch pad, but is not limited thereto. For example, the manipulation panel 50 may be implemented by an input device, e.g., a joystick, a track ball, a knob, and a dial.

The manipulation panel 50 may further include a sub display unit 51. The sub display unit 51 may be provided on one side of the manipulation panel 50 to display information related to a manipulation of the ultrasonic imaging apparatus1.

For example, the sub display unit 51 may display menus and guidance needed for setting the ultrasonic imaging apparatus1 and may display current setting of the ultrasonic imaging apparatus1.

The sub display unit 51 may be implemented by a Liquid Crystal Display (LCD), a Light Emitting Diodes (LED), an Organic Light Emitting Diodes (OLED) or a touch panel. When the sub display device 51 is implemented by a touch panel, the user may input a control command by touching the sub display unit 51.

The main display unit 60 may display an ultrasound image and information related to an operation of the ultrasonic imaging apparatus 1. For example, the main display unit 60 may display a volume image of fetus or an image about a reference plane extracted from the volume image.

The main display unit 60 may include a plurality of display units 61 and 62, and the main display unit 61 and 62 may display different ultrasound images. For example, a first display unit 61 may display a volume image of fetus, and a second display unit 62 may display a plurality of reference plane images extracted from the volume image.

The display unit 61 and 62 may employ a display device, such as a Plasma Display Panel (PDP), a Liquid Crystal Display (LCD), a Light Emitting Diodes (LED), an Organic Light Emitting Diodes (OLED), or an Active Matrix Organic Light Emitting Diodes (AMOLED).

The ultrasonic imaging apparatus 1 may include a communication unit 120, a storage 130, and a processor 200.

The communication unit 120 may communicate with an external device and a server via a network 3. The communication unit 120 may transmit/receive data to/from a hospital server 4 or another medical apparatus 5 in the same hospital connected by Picture Archiving and Communication System (PACS). The communication unit 120 may communicate data according to Digital Imaging and Communications in Medicine (DICOM).

Particularly, the communication unit 120 may transmit/receive data related to diagnosis of an object, such as an ultrasound image, an ultrasound data, and a Doppler data of the object 1 via the network 3, and also may transmit/receive a medical image, such as a CT image, a MRI image, acquired by other medical apparatus 5. Further, the communication unit 120 may receive information about diagnostic history and treatment schedule of patients from the server 4 and may use for the diagnosis of the object 1. The communication unit 120 may perform data communication with a portable terminal 6 of a doctor or a patient as well as the hospital server 4 and the medical apparatus 5 provided in the hospital.

The communication unit 120 may send/receive data to/from the hospital server 4, the medical apparatus 5 or the portable terminal 6 by being connected to the network 3 via a wire or a wireless communication. The communication unit 120 may include one or more component, e.g., a local area communication module 121, a wired communication module 122, and a mobile communication module 123, to allow communication with an external device.

The local area communication module 121 may represent a module for local area communication within a certain distance. A local area communication technology according to an embodiment of the present disclosure may include Wireless LAN, Wi-Fi, Bluetooth, zigbee, Wi-Fi Direct (WFD), ultra wideband (UWB), Infrared Data Association (IrDA), Bluetooth Low Energy (BLE), Near Field Communication (NFC), but is not limited thereto.

The wired communication module 122 may represent a module for a communication by using an electric signal or an optical signal. A wired communication technology according to an embodiment of the present disclosure may include a pair cable, a coaxial cable, a fiber optic cable, and an Ethernet cable.

The mobile communication module 123 may transmit/receive a radio signal to/from at least one of a base station, an external terminal and a server on the mobile communication network. The radio signal may include a voice call signal, a video communication call signal or data which is various according to transmission/reception of text/multimedia message.

The storage 130 may store various information needed for operations of the ultrasonic imaging apparatus 1. For example, the storage 130 may store an operation system of the ultrasonic imaging apparatus 1, and an application needed for operations of the ultrasonic imaging apparatus 1.

The storage 130 may store data generated by the operation of the ultrasonic imaging apparatus 1. For example, the storage 130 may store volume data outputted from the data acquisition unit 110, and volume images generated based on the volume data. In addition, the storage 130 may store an image corresponding to a reference plane extracted from the volume data.

The storage 130 may include high-speed random access memory, magnetic disk, SRAM, DRAM, or ROM but is not limited thereto.

The storage 130 may be detachably installed on the ultrasonic imaging apparatus1. For example, the storage 130 may include Compact Flash (CF) Card, Secure Digital (SD) Card, Smart Media (SM) Card, Multimedia Card (MMC), or Memory Stick, but is not limited thereto.

The processor 200 may generally control operations of the ultrasonic imaging apparatus 1. Particularly, the processor 200 may control operations of the display unit 60, the manipulation panel 50, the communication unit 120, the storage 130 and the data acquisition unit 110 according to a control command, which is inputted through the manipulation panel 50.

The processor 200 may be implemented by array of multiple logic gates, a combination with universal microprocessors 200 and memory in which programs implemented in the microprocessors 200 are stored. For example, the processor 200 may be implemented as a central processing unit (CPU) and a graphic processing unit (GPU), but is not limited thereto.

The processor 200 may generate a volume image based on a volume data. The processor 200 may generate an ultrasound image by a scan conversion process of a volume data. The ultrasound image generated in the process 200 may include an Amplitude mode (A mode), a Brightness mode (B mode), a Doppler mode (D mode), an Elastography mode (E mode), and a Motion mode (M mode), but is not limited thereto.

The processor 200 may generate a plurality of 2D ultrasound images, and 3D volume images by applying data interpolation to the 2D ultrasound images.

The processor 200 may perform pre-process of volume data before generating a volume image. For example, the pre-processing configured to remove a noise included in the volume data, and configured to normalize a volume data may be performed.

The processor 200 may extract a certain reference plane from a volume data outputted from the data acquisition unit 110, and may generate a cross-sectional image corresponding to the reference plane.

The reference plane may be a certain cross-section of an object, and may represent a cross-section where test items needed for the diagnosis of an object are prominently displayed. The test items needed for the diagnosis of the object may be different depending on a diagnostic region and a diagnostic target, and the reference plane may also be determined depending on a diagnostic region and a diagnostic target. Hereinafter a reference plane used for the diagnosis of fetal head will be described.

Figure 3:
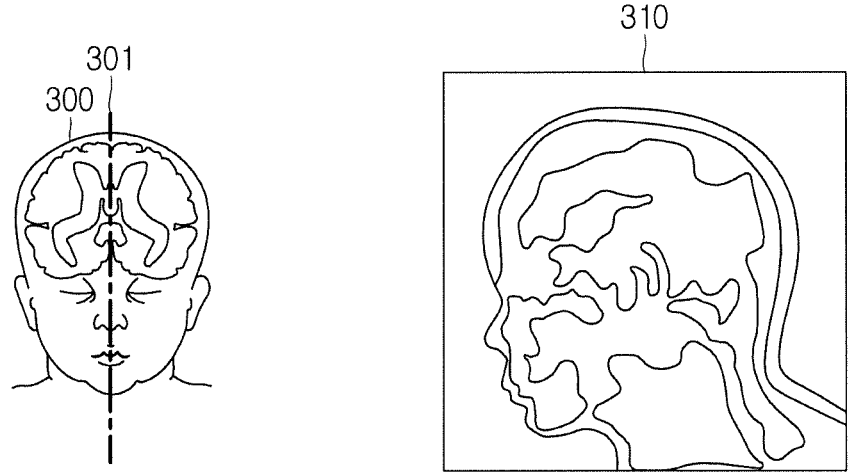
FIGS. 3 and 4 are views schematically illustrating an image of a reference plane of fetus.
Figure 4:
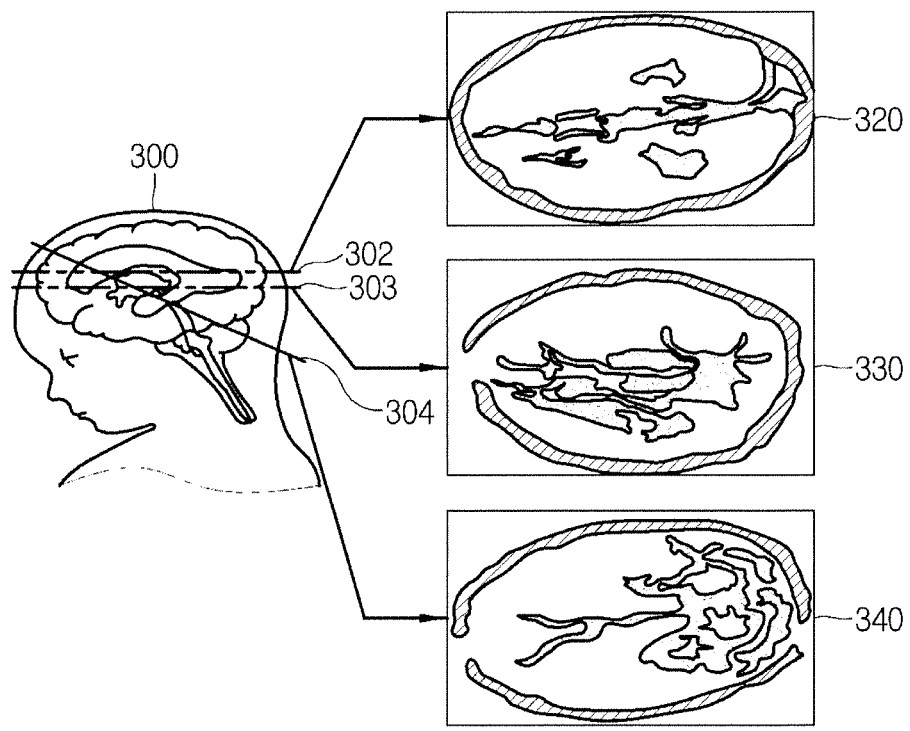

FIGS. 3 and 4 are views schematically illustrating an image of a reference plane of fetus, FIG. 3 schematically illustrates a mid-sagittal plane, and FIG. 4 schematically illustrates a cross section.

In order to diagnose a fetal head, test items, such as biparietal diameter (BPD), occipitofrontal diameter (OFD), head circumference (HC) of fetal head 300, Posterior Cerebral Ventricle Diameter (Vp), abdominal circumference (AC), femur length (FL), femur length (FL), a location of thalamus (T), Doppler information of vessels, Transverse cerebellar Diameter (TCD), and Cisterna Magna (CM) may be needed.

A reference plane for the diagnosis of fetal head 300 may be at least one of a Mid Sagittal Plane (MSP) 310, a Trans-Ventricular Plane (TVP) 320, a Trans-Thalamic Plane (TTP) 330, and a Trans-Cerebellar Plane (TCP) 340, as illustrated in FIGS. 3 and 4.

As illustrated in FIG. 3, among sagittal planes, the Mid Sagittal Plane (MSP) 310 may represent a plane corresponding to a line segment 301 dividing a center of the fetal head 300. The Mid Sagittal Plane (MSP) 310 may be used to detect the Trans-Ventricular Plane (TVP) 320, the Trans-Thalamic Plane (TTP) 330, and the Trans-Cerebellar Plane (TCP) 340, but is not limited thereto.

As illustrated in FIG. 4, among axial planes of the fetal head 300, the Trans-Ventricular Plane (TVP) 320 may represent a plane corresponding to a line segment 302 passing through ventricle, the Trans-Thalamic Plane (TTP) 330 may represent a plane corresponding to a line segment 303 passing through thalamus, and the Trans-Cerebellar Plane (TCP) 340 may represent a plane corresponding to a line segment 304 passing through cerebellum.

The Trans-Thalamic Plane (TTP) 330 may be used to measure test items, such as head circumference (HC) of fetal head 300, biparietal diameter (BPD) and occipitofrontal diameter (OFD). The Trans-Cerebellar Plane (TCP) 340 may be used to measure test items, such as Transverse cerebellar Diameter (TCD), and Cisterna Magna (CM). The Trans-Ventricular Plane (TVP) 320 may be used to measure test items, such as Posterior Cerebral Ventricle Diameter (Vp).

That is, to accurately diagnose the object, a reference plane in which test items are displayed may be needed to be accurately extracted. The processor 200 may determine whether the acquisition position of a volume data is within a predetermined allowable range before extracting a reference plane.

The predetermined allowable range may represent a location which is appropriate to extract a plurality of reference planes, and may be defined based on a relationship between a plurality of reference planes.

Figure 5:
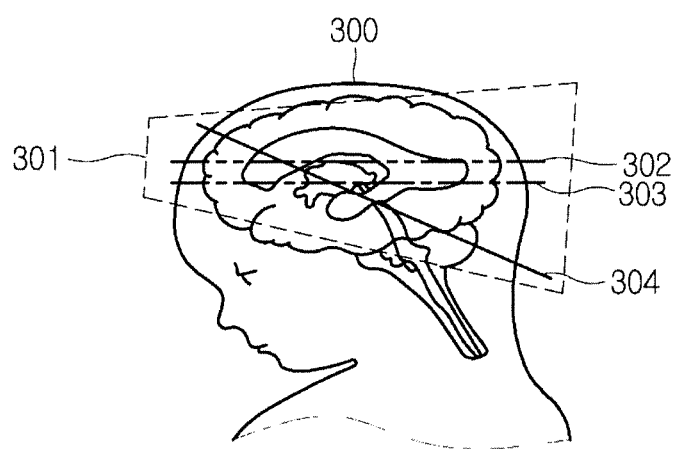
FIG. 5 is a view schematically illustrating an example of an allowable range.

FIG. 5 is a view schematically illustrating an example of an allowable range and FIGS. 6A-6D are views schematically illustrating an example of landmark information.

Referring to FIGS. 4 and 5, when an object is fetal head 300, an allowable range 301 may be defined to include the Trans-Ventricular Plane (TVP) 320 and the Trans-Cerebellar Plane (TCP) 340.

The line segment 303 passing through thalamus corresponding to the Trans-Thalamic Plane (TTP) 330 may be placed between the line segment 302 passing through ventricle corresponding to the Trans-Ventricular Plane (TVP) 320 and the line segment 304 passing through cerebellum corresponding to the Trans-Cerebellar Plane (TCP) 340. The Mid Sagittal Plane (MSP) 310 may have an orthogonal relationship with the Trans-Ventricular Plane (TVP) 320 and the Trans-Cerebellar Plane (TCP) 340, and thus when the allowable range is defined as the Trans-Ventricular Plane (TVP) 320 and the Trans-Cerebellar Plane (TCP) 340, all kinds of reference planes may be extracted.

In addition, since a reference plane is well known to a user and the reference plane is a location where an ultrasound signal is accurately acquired, scanning of fetal brain may be easily performed by setting the allowable range 301 to include the plurality of reference planes. In other words, the allowable range 301 may include at least two reference planes among the plurality of reference planes.

The processor 200 may determine whether the acquisition position of the volume data, which is acquired by using pre-stored landmark information, is within the allowable range.

The pre-stored landmark information may represent information about landmark indicating anatomical features of an object, that is landmark information may include anatomical features of Cavum septum pellucidum (CSP), Cerebellum, Choroid plexus, Lateral ventricle, Cisterna magna, and Thalami.

Particularly, the landmark information may be a certain cross-section of an object. That is, the landmark information may include information, e.g., a shape, a size, and a location of a landmark, which are existed in the certain cross-section, and a correlation with another landmark.

There may be no limitation to a cross-section of an object, which is to be landmark information, but as illustrated in FIGS. 6A-6D, landmark information may be related to a reference plane indicating anatomical features of an object clearly.

Figure 6A:
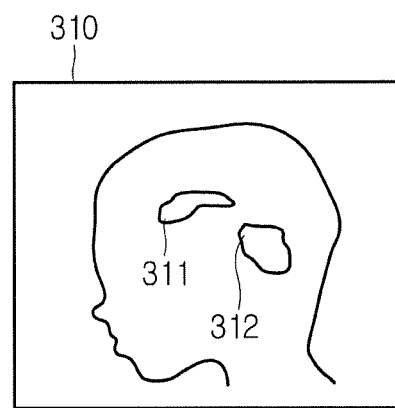
FIGS. 6A-6D are views schematically illustrating an example of landmark information.
Figure 6B:
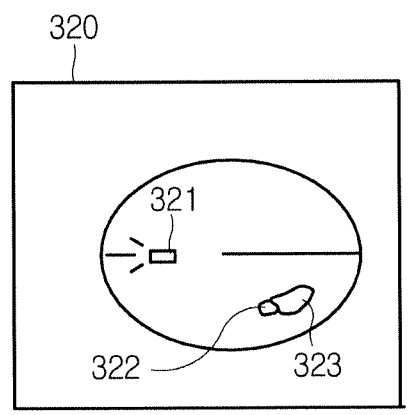
Figure 6C:
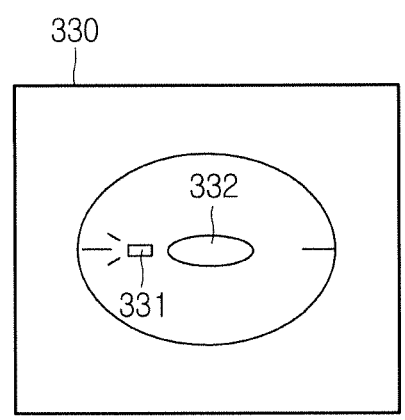
Figure 6D:
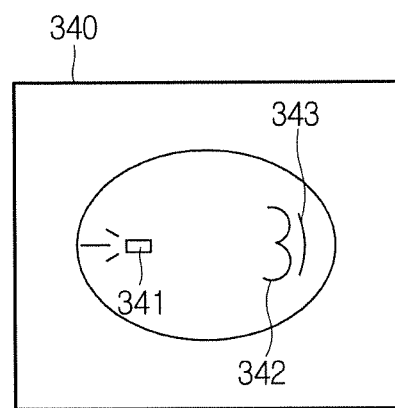

Particularly, the landmark information may include at least one of landmark information about the Mid Sagittal Plane (MSP) 310, as illustrated in FIG. 6A, landmark information about the Trans-Ventricular Plane (TVP) 320, as illustrated in FIG. 6B, landmark information about the Trans-Thalamic Plane (TTP) 330, as illustrated in FIG. 6C, and landmark information about the Trans-Cerebellar Plane (TCP) 340, as illustrated in FIG. 6D.

Landmark information about each plane may include landmark commonly existed in the plurality of reference planes and landmark distinctively existed on a single reference plane.

As illustrated in FIGS. 6A-6D, landmark information may include Cavum septum pellucidum (CSP), which is commonly existed on each reference plane, as common landmarks 311, 321, 331, and 341. However, the shape, the size, the position of the Cavum septum pellucidum (CSP) may vary according to the reference plane.

In addition, the Mid Sagittal Plane (MSP) 310 may include the Cerebellum 312 as a distinctive landmark, and the Trans-Ventricular Plane (TVP) 320 may include the lateral ventricle 323 and the choroid plexus 322 as a distinctive landmark, the Trans-Thalamic Plane (TTP) 330 may include the Thalami 332 as a distinctive landmark, and the Trans-Cerebellar Plane (TCP) 340 may include the Cerebellum 342 and the cisterna magna 343 as a distinctive landmark.

The acquisition position of the volume data may be determined based on the landmark information. Particularly, the processor 200 may extract at least one sample plane from the volume data, may determine whether an acquisition position of a volume data is within an allowable range by comparing a similarity between landmark of the sample plane and landmark information of pre-stored reference plane, and may extract a reference plane of the volume data when the acquisition position of the volume data is within an allowable range. Hereinafter the extraction of the reference plane by using landmark information will be described in detail.

Figure 7:
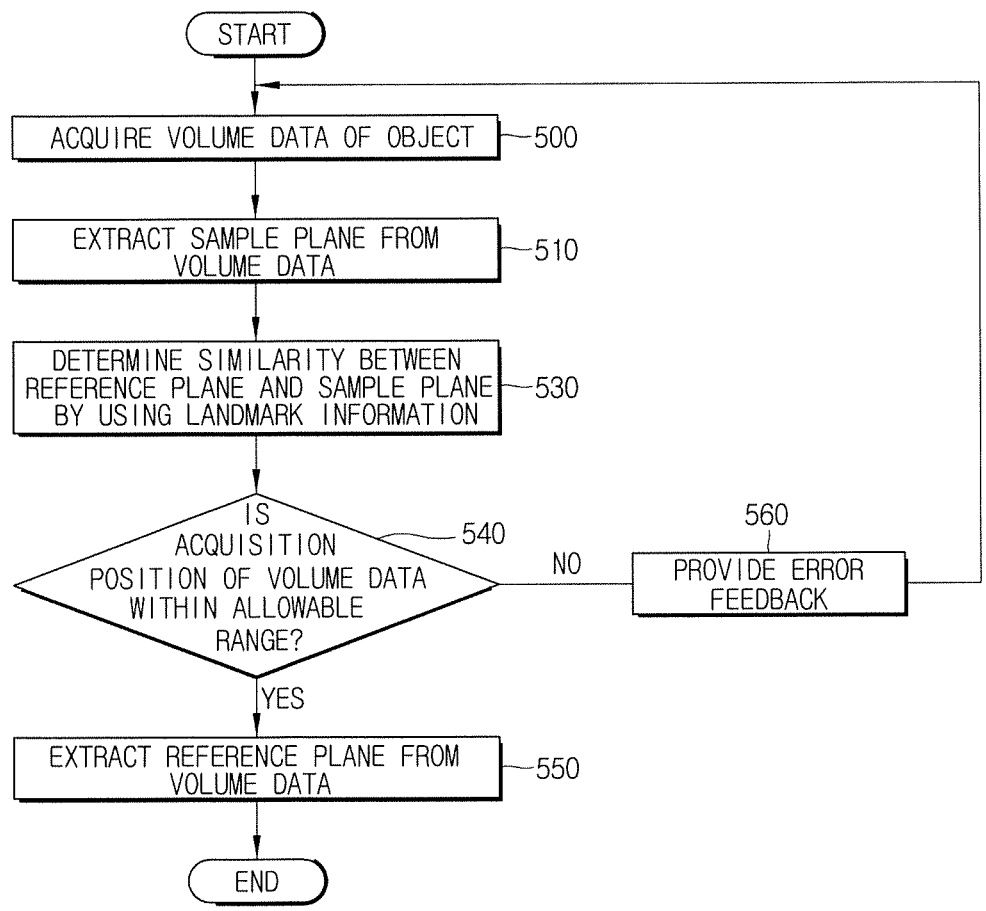
FIG. 7 is a flowchart illustrating an example of a method of extracting reference plane by an ultrasonic imaging apparatus according to an embodiment of the present disclosure.
Figure 8:
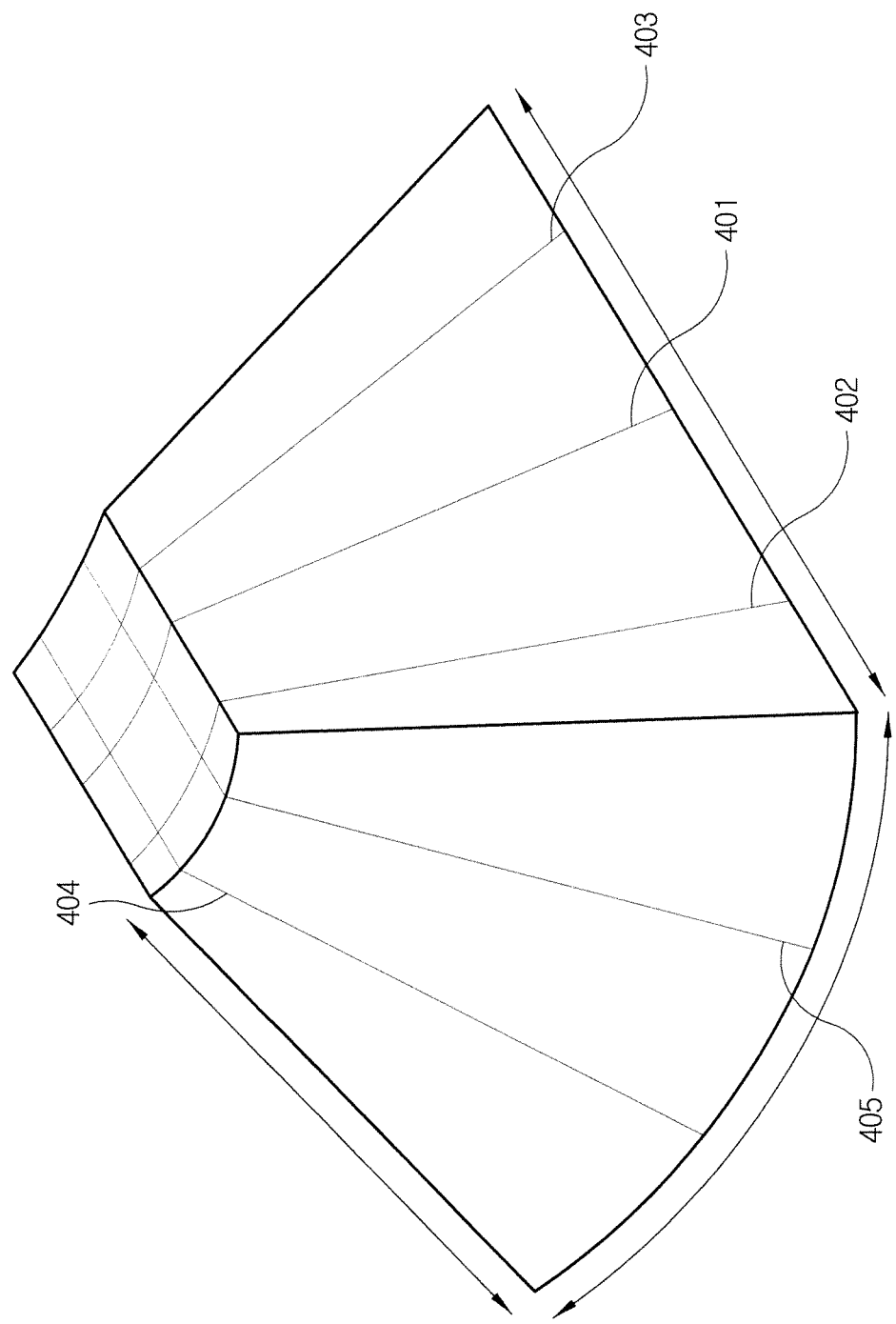
FIG. 8 is a view illustrating a sample plane extracted from a volume data.

FIG. 7 is a flowchart illustrating an example of a method of extracting a reference plane by an ultrasonic imaging apparatus according to an embodiment of the present disclosure and FIG. 8 is a view illustrating a sample plane extracted from a volume data.

Referring to FIG. 7, the ultrasonic imaging apparatus 1 may acquire a volume data of an object (510), and may extract a sample plane from the volume data (520). The sample plane may represent a cross-section extracted from the volume data, and thus a plurality of the sample planes 401, 402, 403, 404 and 405 may be extracted from the volume data, as illustrated in FIG. 8.

Among the volume data, a plane where features are remarkably illustrated may be extracted as the sample plane 401, 402, 403, 404 and 405. For example, the processor 200 may extract a plane where the difference of brightness is remarkably displayed, or a plane having pre-determined brightness value from the volume data as the sample planes 401, 402, 403, 404 and 405.

The ultrasonic imaging apparatus 1 may determine a similarity between the reference plane and the sample planes 401, 402, 403, 404 and 405 by using landmark information (530). As mentioned above, since the landmark information may include landmark about the reference plane, the processor 200 may compare the sample planes 401, 402, 403, 404 and 405 and the reference plane by using landmark information.

Particularly, the processor 200 may detect an outline in the sample planes 401, 402, 403, 404 and 405. The outline may be detected through an edge mask, such as Sobel mask, Prewitt mask, Robert mask, Canny mask, but is not limited thereto.

The processor 200 may sequentially determine a similarity between each sample plane 401, 402, 403, 404 and 405 and the reference plane by comparing an outline detected in the sample planes 401, 402, 403, 404 and 405 with landmark corresponding to the reference plane. The processor 200 may determine the similarity between each sample plane 401, 402, 403, 404 and 405 and the reference plane by performing conversion of scale on the landmark corresponding to the reference plane or by rotating the landmark corresponding to the reference plane.

At this time, the landmark information may be related to a plane corresponding to a plane used to define an allowable range. For example, when the allowable range is defined as the Trans-Ventricular Plane (TVP) 320 and the Trans-Cerebellar Plane (TCP) 340, landmark information may include a landmark about Trans-Ventricular Plane (TVP), as illustrated in FIG. 6B, and a landmark about Trans-Cerebellar Plane (TCP), as illustrated in FIG. 6D. In addition, the processor 200 may compare a plurality of extracted planes 401, 402, 403, 404 and 405 with landmark about the Trans-Ventricular Plane (TVP) 320, and then may determine a similarity between each extracted plane 401, 402, 403, 404 and 405 and the Trans-Ventricular Plane (TVP) 320. The processor 200 may compare a plurality of extracted planes 401, 402, 403, 404 and 405 with landmark about the Trans-Cerebellar Plane (TCP) 340, and then may determine a similarity between each extracted plane 401, 402, 403, 404 and 405 and Trans-Cerebellar Plane (TCP) 340.

The ultrasonic imaging apparatus 1 may determine whether the acquisition position of the volume data is within the allowable range based on the similarity (540). Particularly, the processor 200 may determine whether the acquisition position is within an allowable range according to the presence of an extracted plane in which a similarity with the reference plane is higher than a threshold, and according to the number of an extracted plane in which a similarity is higher than a threshold.

For example, when an extracted plane having a similarity more than the threshold with a landmark about the Trans-Ventricular Plane (TVP) 320 of FIG. 6B, and an extracted plane having a similarity more than the threshold with a landmark about the Trans-Cerebellar Plane (TCP) 340 of FIG. 6D are existed, the acquisition position of the volume data may be determined to be within an allowable range.

When the acquisition position of the volume data is determined to be within the allowable range (YES of 540), the ultrasonic imaging apparatus 1 may extract a plurality of reference planes from the volume data. For the extraction of the reference plane, information related to a similarity between the extracted plane determined in step 530 and the reference plane may be used.

In addition, for the extraction of the reference plane, landmark information about the aforementioned reference plane may be used. Particularly, the processor 200 may extract a plane having a highest similarity with a landmark corresponding to a reference plane, as a reference plane, by searching an extracted plane having a high similarity with a reference plane and an adjacent plane. In addition, the processor 200 may extract another reference plane from a single reference plane based on an anatomical relationship between a plurality of reference planes.

For example, when a first extracted plane 401 has a high similarity with the Trans-Ventricular Plane (TVP) 320, that is a reference plane, the processor 200 may extract the Trans-Ventricular Plane (TVP) 320 of the object by searching a plane corresponding to the Trans-Ventricular Plane (TVP) 320 in a position adjacent to the first extracted plane 401. At this time, when the Trans-Ventricular Plane (TVP) 320 is extracted, landmark information about the Trans-Ventricular Plane (TVP) 320 may be used.

When the Trans-Ventricular Plane (TVP) 320 is detected, the processor 200 may extract the Trans-Cerebellar Plane (TCP) 340 in a position which is rotated by a certain angle with respect to Cavum septum pellucidum (CSP), which is a common landmark existed in the reference plane, and may extract a plane crossing Cavum septum pellucidum (CSP) while being perpendicular to the Trans-Ventricular Plane (TVP) 320, as the Mid Sagittal Plane (MSP) 310.

Meanwhile, when a similarity between the sample plane and the reference plane is equal to or lower than a threshold (NO of 540), the ultrasonic imaging apparatus 1 may provide an error feedback and then return to step 510.

By determining whether the acquisition position of the volume data is within the allowable arrange prior to extracting a reference plane, load of the extraction of the reference plane may be reduced. In addition, a plurality of reference planes is automatically extracted from the volume data by using pre-stored landmark information so that a user may easily diagnose fetus.

Meanwhile, since there are difficulties in directly observing fetus, and a position and a posture of fetus are changed as time passes, it may be difficult for a user to determine whether an acquisition position of a volume data is within an allowable range. The processor 200 may provide feedback to a user according to the acquisition position of the volume data. Hereafter a method of providing feedback according to the acquisition position of the volume data will be described in detail.

Figure 9:
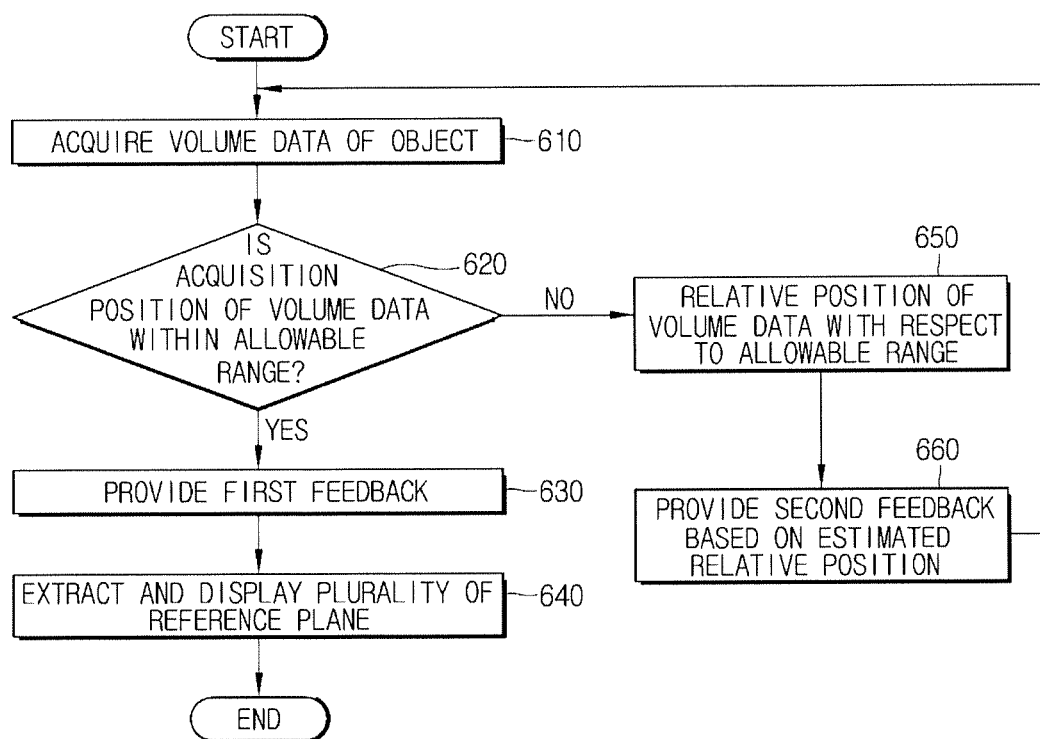
FIG. 9 is a flowchart illustrating an example of a method of providing feedback of an ultrasonic imaging apparatus according to an embodiment of the present disclosure.
Figure 10A:
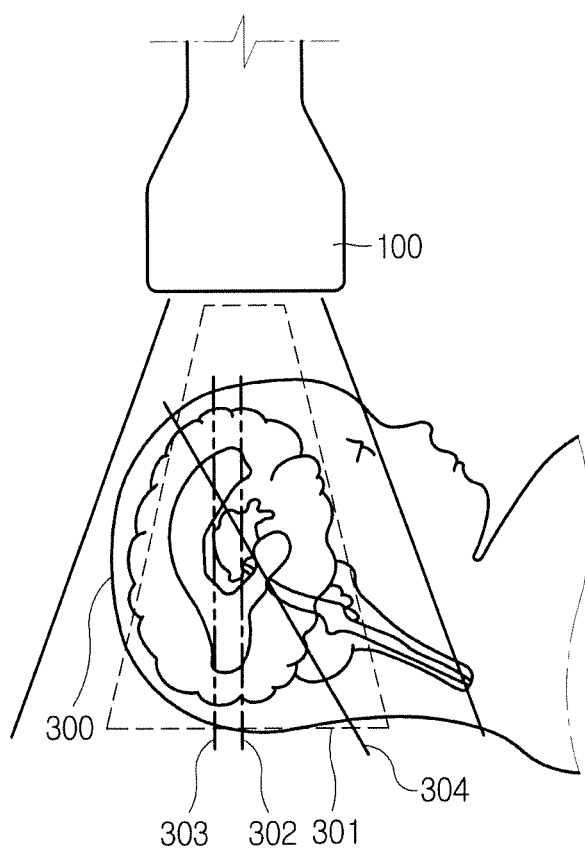
FIGS. 10A-10C are views schematically illustrating a relation between a volume data and an allowable range.
Figure 10B:
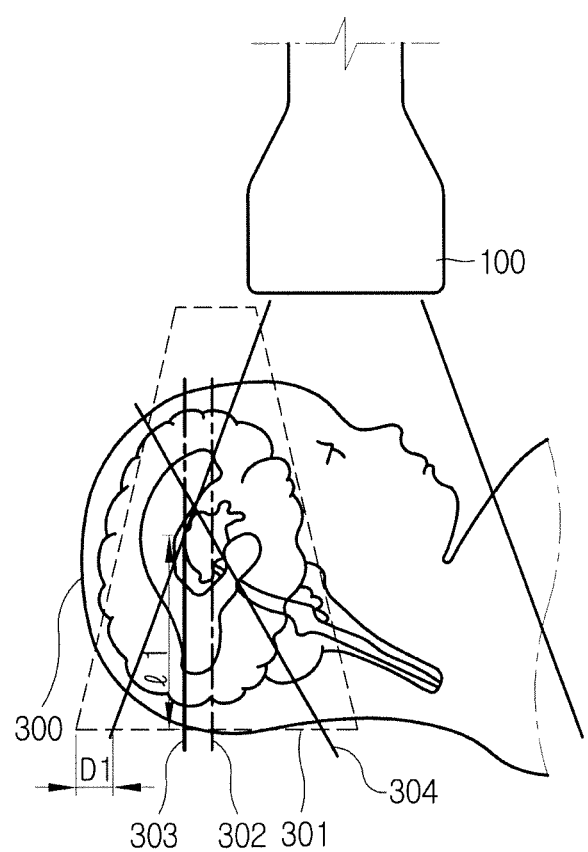
Figure 10C:
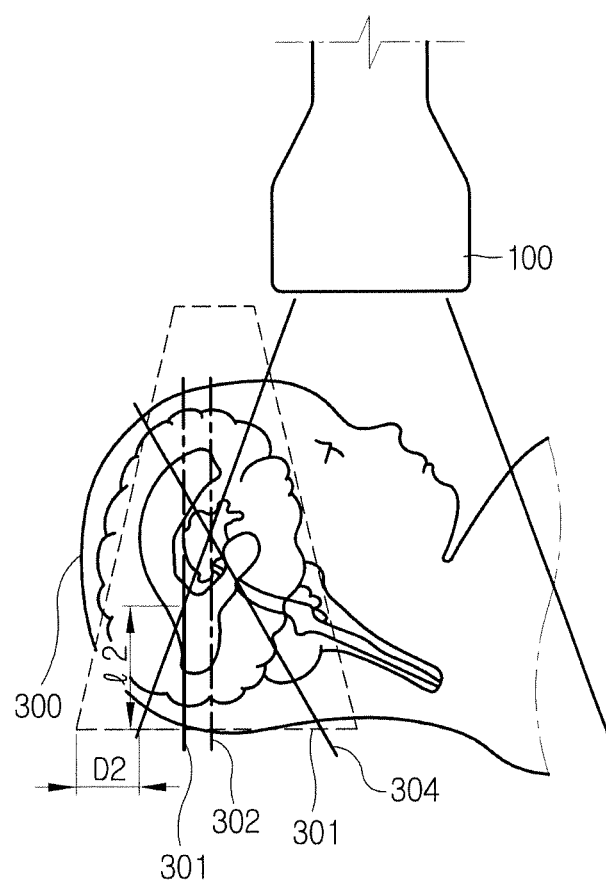

FIG. 9 is a flowchart illustrating an example of a method of providing feedback of an ultrasonic imaging apparatus according to an embodiment of the present disclosure and FIGS. 10A-10C are views schematically illustrating a relation between a volume data and an allowable range.

Referring to FIG. 9, the ultrasonic imaging apparatus 1 may acquire a volume data (610). The ultrasonic imaging apparatus 1 may determine whether an acquisition position of the volume data is within an allowable range (620). As mentioned in FIG. 7, whether the acquisition position of the volume data is within the allowable range may be determined by comparing a sample plane of the volume data with the pre-stored landmark information, but is not limited thereto.

When the acquisition position of the volume data is within the allowable range (YES of 620), the ultrasonic imaging apparatus 1 may provide a first feedback (630), may extract a plurality of reference planes, and then may display the extracted reference plane (640). Particularly, as illustrated in FIG. 10A, when the volume data acquired by the ultrasonic probe 100 includes the allowable range, by providing the first feedback, it will be informed to a user that the position of the ultrasonic probe 100 is appropriate.

The first feedback may be provided in a tactile, an acoustic and visual manner. For example, the processor 200 may control the ultrasonic probe 100 to generate a pre-set haptic, may control the main display unit 60 or the sub display unit 51 to display a pre-set screen, or may control a speaker provided on the ultrasonic imaging apparatus 1 to generate a pre-set sound.

When the acquisition position of the volume data is not within the allowable range (NO of 620) the ultrasonic imaging apparatus 1 may estimate a relative position of the volume data with respect to the allowable range (650). The processor 200 may estimate the relative position of the volume data based on a similarity between a sample plane extracted from the volume data and a pre-stored landmark.

As illustrated in FIG. 10B, when a relative position between an allowable range and the volume data is D1, I1 of the reference plane may be existed in the volume data, and as illustrated in FIG. 10C, when a relative position between an allowable range and the volume data is D2 (D2>D1), I2 of the reference plane may be existed in the volume data. In other words, as the acquisition position of the volume data is far from the allowable range, the similarity between the sample plane and the pre-stored landmark may be lowered. Therefore, the processor 200 may estimate a relative distance between the acquisition position of the volume data and the allowable range according to the similarity between the sample plane and the pre-stored landmark.

The ultrasonic imaging apparatus 1 may provide a second feedback based on the estimated relative position (660), and then return to a step 610. The second feedback may be provided in a tactile, an acoustic and visual manner, as like the first feedback, but the second feedback may be provided differently from the first feedback to avoid confusion with the first feedback. For example, the second feedback may provide a haptic having different from the haptic of the first feedback.

In addition, the processor 200 may differently provide the second feedback according to the estimated relative position. For example, as the relative position is closer, the size of the generated haptic may be reduced, and as the relative position is far, the size of the generated haptic may be increased. In addition, the processor 200 may control the display unit 60 or the sub display unit 51 so that the second feedback is displayed to be small and blur as the relative position is closer, and the second feedback is displayed to be big and clear as the relative position is far.

A different feedback from each other may be provided according to the acquisition position of the volume data so that a user may easily acquire the volume data corresponding to the allowable range.

Figure 11:
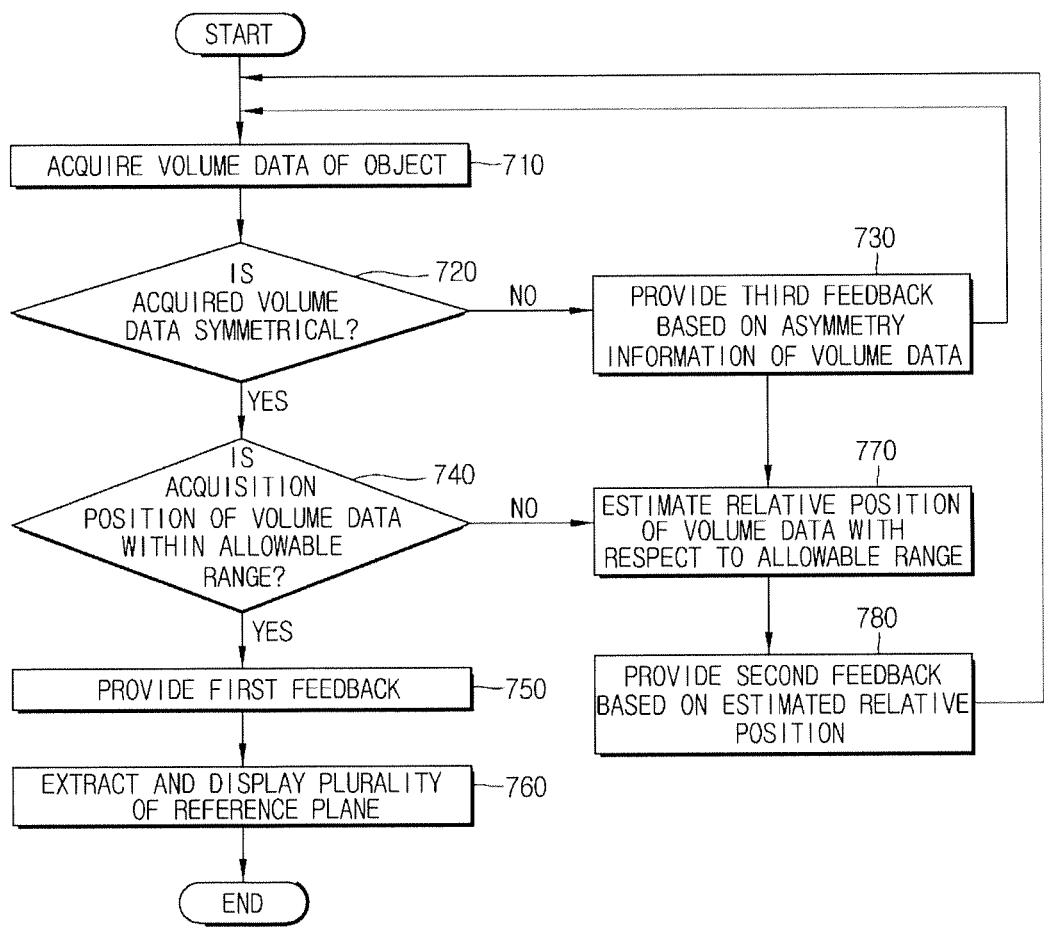
FIG. 11 is a flow chart illustrating another method of a method of providing feedback of an ultrasonic imaging apparatus according to an embodiment of the present disclosure.
Figure 12A:
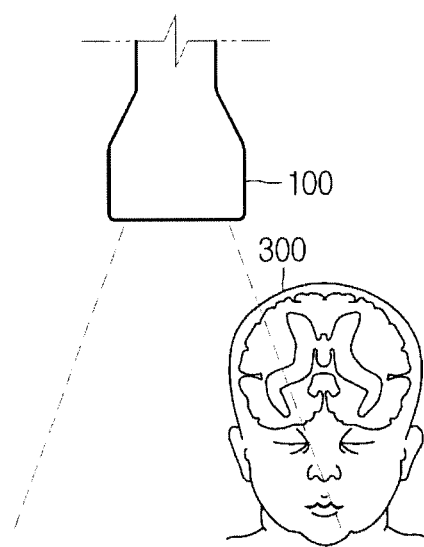
FIGS. 12A-12C are views schematically illustrating the symmetry of a volume data.
Figure 12B:
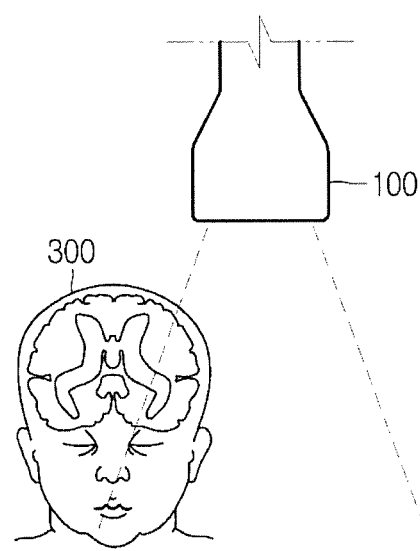
Figure 12C:
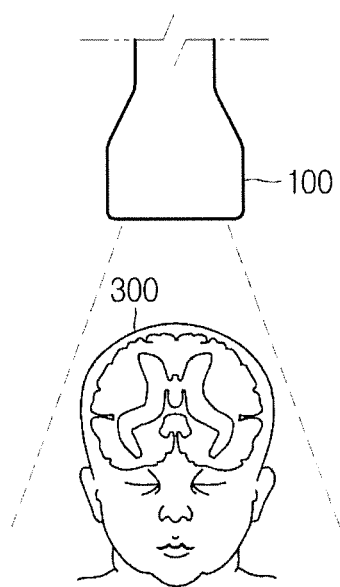

FIG. 11 is a flow chart illustrating another method of a method of providing feedback of an ultrasonic imaging apparatus according to an embodiment of the present disclosure and FIGS. 12A-12C are views schematically illustrating the symmetry of a volume data.

Referring to FIG. 11, the ultrasonic imaging apparatus 1 may acquire a volume data (710). The ultrasonic imaging apparatus 1 may determine whether the acquired volume data is symmetrical (720). The processor 200 may determine whether the object is asymmetrically placed on an edge of the volume data, as illustrated in FIGS. 12A and 12B or whether the object is symmetrically placed on the center of the volume data, as illustrated in FIG. 12C.

Particularly, the processor 200 may extract at least one plane from the volume data, and may determine whether the volume data is symmetrically by determining the symmetry of the extracted plane. At this time, the extracted plane may be the same as the aforementioned sample plane, but is not limited thereto.

When the volume data is asymmetrical (NO of 720) the ultrasonic imaging apparatus 1 may provide a third feedback based on asymmetry information of the volume data (730). The third feedback may be provided in a tactile, an acoustic and visual manner, as like the first feedback, but the third feedback may be provided differently from the first and second feedback to avoid confusion with the first and second feedback.

The third feedback may be provided in a different manner according to the direction of the asymmetry. Particularly, a feedback in a case in which the object is placed in the position of FIG. 12A, and a feedback in a case in which the object is placed in the position of FIG. 12B may be different.

When the volume data is symmetrical, the ultrasonic imaging apparatus 1 may determine whether the acquisition position of the volume data is within the allowable range (740).

When the acquisition position of the volume data is within the allowable range (YES of 740), the ultrasonic imaging apparatus 1 may provide the first feedback (750), and may extract and display a plurality of reference planes (760).

When the acquisition position of the volume data is out of the allowable range (NO of 740), the ultrasonic imaging apparatus 1 may estimate a relative position of the volume data with respect to the allowable range (770), may provide the second feedback based on the estimated relative position (780), and may return to a step 710.

Unlike FIG. 1, the ultrasonic imaging apparatus 1 may be implemented by a portable ultrasonic apparatus configured to be hand-held when moving at a long distance. The portable ultrasonic apparatus 1 may be a PACS viewer, a smart phone, a lap top computer, a personal digital assistant (PDA), and a tablet personal computer, but is not limited thereto.

In addition, FIG. 1 illustrates that the ultrasonic probe 100 is implemented by a wired probe, but is not limited thereto. For example, the ultrasonic probe 100 may be implemented by a wireless probe.

In FIGS. 4 to 12, fetal head is illustrated as an object, but an object is not limited thereto.

Figure 13:
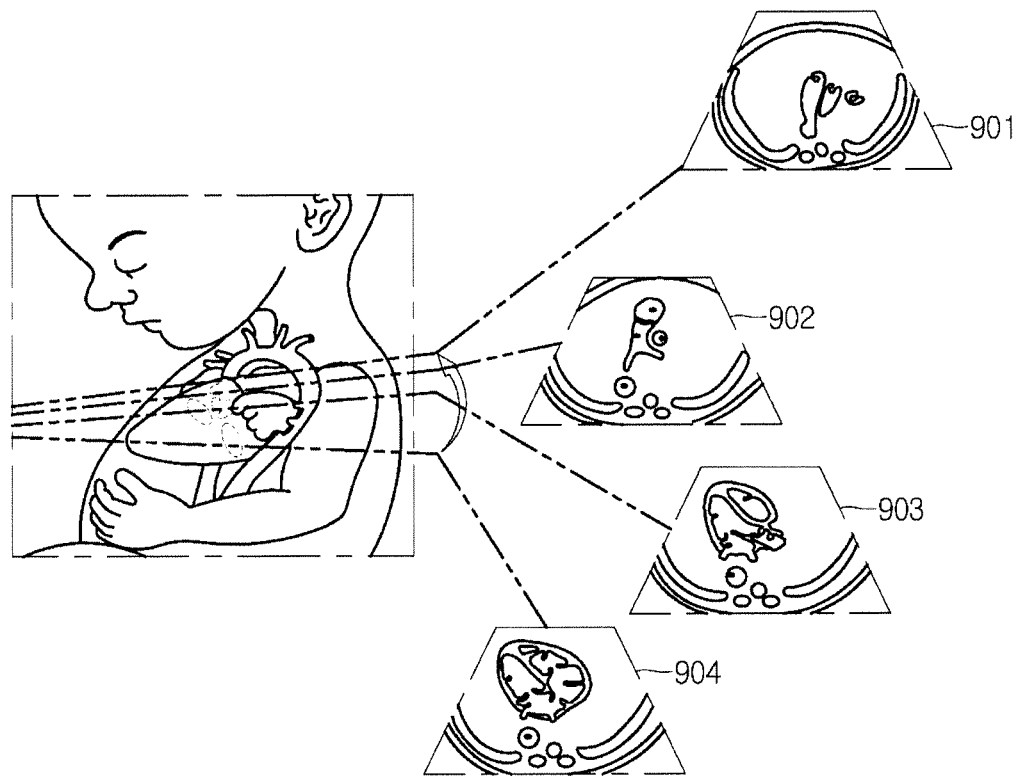
FIG. 13 is a view schematically illustrating a reference plane when an object is a heart.
Figure 14:
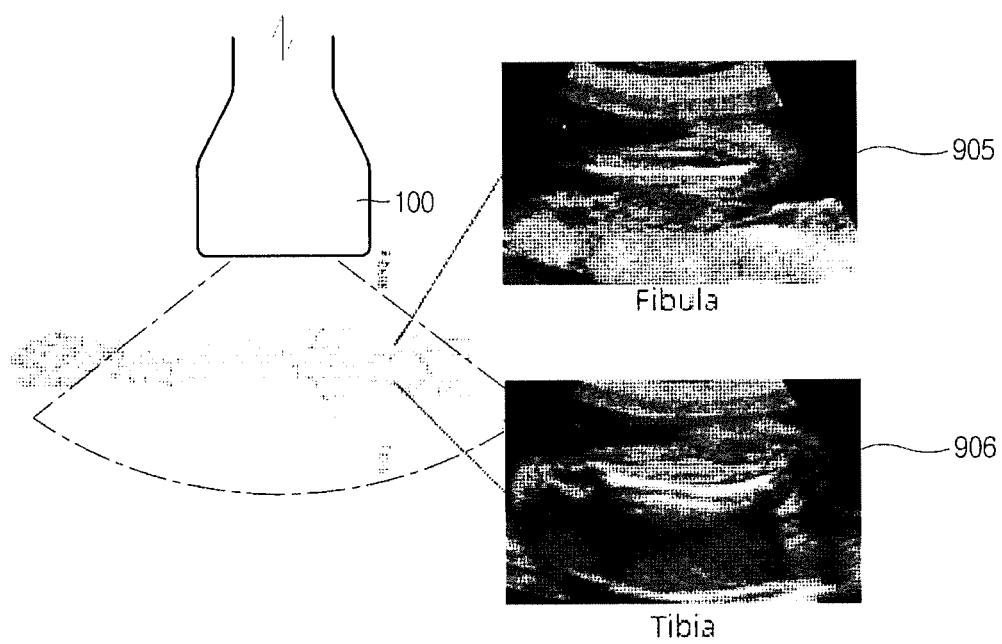
FIG. 14 is a view schematically illustrating a reference plane when an object is legs.

FIG. 13 is a view schematically illustrating a reference plane when an object is a heart and FIG. 14 is a view schematically illustrating a reference plane when an object is legs.

The object may be a fetal heart, as illustrated in FIG. 13. When the object is the fetal heart, a reference plane may be three vessel view (3VT), Right ventricular outflow tract (RVOT), and Four-chamber view, and fetal atrium and fetal ventricles may be used as landmark information.

In addition, the object may be fetal legs, as illustrated in FIG. 14. When the object is fetal legs, a cross-section of fibula or a cross-section of tibia may be a reference plane, and fibula and tibia may be used landmark information.

The control method of the ultrasonic imaging apparatus 1 may be implemented as a computer readable code on a computer readable recording medium. The computer readable recording medium may include various kinds of recording medium in which data decipherable by the computer system is stored. For example, there may be a Read Only Memory (ROM), a Random Access Memory (RAM), a magnetic tape, a magnetic disk, a flash memory, and an optical data storage 130. In addition, the medium may be distributed to computer systems over a network, in which computer-readable code may be stored and executed in a distributed manner.

As is apparent from the above description, the ultrasound imaging apparatus and the control method thereof, the load of the extraction of the reference plane may be reduced by determining whether the acquisition position of the volume data is within the allowable range, prior to extracting the reference plane. In addition, the plurality of reference planes may be automatically extracted from the volume data by using pre-stored landmark information so that a user may easily diagnose a fetus.

In addition, the feedback may be provided to the user according to the acquisition position of the volume data so that the operation of the ultrasonic probe may be easily performed by the user.

Although a few embodiments of the present disclosure have been shown and described, it would be appreciated by those skilled in the art that changes may be made in these embodiments without departing from the principles and spirit of the disclosure, the scope of which is defined in the claims and their equivalents.

DESCRIPTION OF NUMERALS

1: ultrasonic imaging apparatus
100: ultrasonic probe
110: data acquisition unit
120: communication unit
130: storage
200: processor

What is claimed is:

1. An ultrasonic imaging apparatus comprising:
   a transmitter and a receiver, wherein the transmitter and the receiver are configured to acquire volume data of an object; and
   a processor configured to:
   extract a plurality of sample planes from the volume data, each sample plane of the plurality of sample planes including a cross-section of the volume data,
   determine a first similarity between each sample plane of the plurality of sample planes and a first pre-stored reference plane,
   determine a second similarity between each sample plane of the plurality of sample planes and a second pre-stored reference plane different from the first pre-stored reference plane,
   determine that an acquisition position of the volume data is within an allowable range when the plurality of sample planes extracted from the volume data includes both a first sample plane having the first similarity with the first pre-stored reference plane higher than a threshold and a second sample plane having the second similarity with the second pre-stored reference plane higher than the threshold, and
   when the acquisition position of the volume data is determined to be within the allowable range, extract from the volume data a first reference plane having a highest first similarity with the first pre-stored reference plane and a second reference plane having a highest second similarity with the second pre-stored reference plane.

2. The ultrasonic imaging apparatus of claim 1, wherein the first and the second reference planes include pre-stored anatomical feature information that comprises at least one of an anatomical feature commonly observable in both the first and the second reference planes or an anatomical feature only observable in either the first or the second reference plane.

3. The ultrasonic imaging apparatus of claim 2, wherein the pre-stored anatomical feature information comprises at least on of Cavum septum pellucidum (CSP), Cerebellum, Choroid plexus, Lateral ventricle, Cisterna magna, or Thalami.

4. The ultrasonic imaging apparatus of claim 1 wherein the processor provides a first feedback to a user when the acquisition position of the volume data is determined to be within the allowable range.

5. The ultrasonic imaging apparatus of claim 4 wherein the first feedback comprises at least one of a tactile feedback, a visual feedback, or an auditory feedback.

6. The ultrasonic imaging apparatus of claim 1 wherein the processor provides a second feedback to a user when the acquisition position of the volume data is determined to be out of the allowable range.

7. The ultrasonic imaging apparatus of claim 6, wherein the processor estimates a relative position of the volume data with respect to the allowable range, and generates the second feedback based on the relative position.

8. The ultrasonic imaging apparatus of claim 7 wherein the second feedback is generated according to the relative position of the volume data with respect to the allowable range.

9. The ultrasonic imaging apparatus of claim 1 wherein the processor provides a third feedback when at least one sample plane among the plurality of sample planes has a first region that is not identical to a second region.

10. The ultrasonic imaging apparatus of claim 1, wherein the first and the second pre-stored reference planes are at least two planes among a trans-thalamic plane (TTP), a trans-ventricular plane (TVP), a trans-cerebellar plane (TCP), or a Mid Sagittal Rane (MSP).

11. The ultrasonic imaging apparatus of claim 1, wherein the first pre-stored reference plane includes at least one anatomical feature, and the second pre-stored reference plane includes another anatomical feature different from the at least one anatomical feature.

12. The ultrasonic imaging apparatus of claim 1, wherein the first and the second pre-stored reference planes include different respective portions of a same anatomical feature.

13. The ultrasonic imaging apparatus of claim 1, further comprising: when the acquisition position of the volume data is determined to be within the allowable range, further extract from the volume data a reference plane having a highest third similarity with a third pre-stored reference plane different from the first and second pre-stored reference planes.

14. The ultrasonic imaging apparatus of claim 1, wherein the second pre-stored reference plane includes a portion of an anatomical feature of the first pre-stored reference plane and is rotated with respect to the first pre-stored reference plane.

15. A control method of an ultrasonic imaging apparatus comprising:

acquiring volume data of an object; extracting a plurality of sample planes from the volume data, each sample plane of the plurality of sample planes including a cross-section of the volume data;

determine a first similarity between each sample plane of the plurality of sample planes and a first pre-stored reference plane;

determine a second similarity between each sample plane of the plurality of sample planes and a second pre-stored reference plane different from the first pre-stored reference plane;

determining that an acquisition position of the volume data is within an allowable range when the plurality of sample planes extracted from the volume data includes both a first sample plane having the first similarity with the first pre-stored reference plane that is higher than a threshold and a second sample plane having the second similarity with the second pre-stored reference plane that is higher than the threshold; and when the acquisition position of the volume data is determined to be within the allowable range, extracting from the volume data a first reference plane having a highest first similarity with the first pre-stored reference plane and a second reference plane having a highest second similarity with the second pre-stored reference plane.

16. The control method of claim 15 further comprising: providing a first feedback to a user when the acquisition position of the volume data is within the allowable range.

17. The control method of claim 15 further comprising: estimating a relative position of the volume data with respect to the allowable range when the acquisition position of the volume data is determined to be out of the allowable range, and generating and providing a second feedback based on the relative position.

18. The control method of claim 15 further comprising: determining whether at least one sample plane among the plurality of sample planes has a first region that is identical to a second region; and providing a third feedback when the at least one sample plane has the first region that is not identical to the second region.

19. The control method of claim 15, wherein the first and the second pre-stored reference planes include at least two planes among a trans-thalamic plane (TTP), a trans-ventricular plane (TVP), a trans-cerebellar plane (TCP), or a Mid Sagittal Plane (MSP).

* * * * *